United States Patent
Yamashita et al.

(10) Patent No.: US 10,160,737 B2
(45) Date of Patent: Dec. 25, 2018

(54) PROCESS FOR PRODUCING POLYVALENT GLYCIDYL COMPOUND

(71) Applicant: SHOWA DENKO K.K., Tokyo (JP)

(72) Inventors: Chika Yamashita, Tokyo (JP); Yoshitaka Ishibashi, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 21 days.

(21) Appl. No.: 15/526,161

(22) PCT Filed: Oct. 28, 2015

(86) PCT No.: PCT/JP2015/080391
§ 371 (c)(1),
(2) Date: May 11, 2017

(87) PCT Pub. No.: WO2016/076112
PCT Pub. Date: May 19, 2016

(65) Prior Publication Data
US 2017/0342042 A1    Nov. 30, 2017

(30) Foreign Application Priority Data
Nov. 12, 2014   (JP) ................... 2014-229965

(51) Int. Cl.
*C07D 301/12*   (2006.01)
*C07D 301/03*   (2006.01)
*C07D 303/12*   (2006.01)
*C07D 303/28*   (2006.01)

(52) U.S. Cl.
CPC ......... *C07D 301/12* (2013.01); *C07D 301/03* (2013.01); *C07D 303/12* (2013.01); *C07D 303/28* (2013.01)

(58) Field of Classification Search
CPC .. C07D 301/12; C07D 303/28; C07D 301/03; C07D 303/12
See application file for complete search history.

(56) References Cited

U.S. PATENT DOCUMENTS

| 4,789,711 | A | 12/1988 | Monnier et al. |
| 8,536,352 | B2 * | 9/2013 | Uchida ............... B01J 31/0237 549/531 |
| 2007/0117993 | A1 | 5/2007 | Hori et al. |
| 2011/0263882 | A1 | 10/2011 | Uchida |

FOREIGN PATENT DOCUMENTS

| JP | 60-060122 A | 4/1985 |
| JP | 63-142019 A | 6/1988 |
| JP | 2004-059573 A | 2/2004 |
| JP | 2010-106009 A | 5/2010 |
| JP | 2014-240377 A | 12/2014 |
| JP | 2014240376 A | 12/2014 |
| JP | 2015127397 A | 7/2015 |
| KR | 10-2011-0063848 A | 6/2011 |
| WO | 2009/014852 A2 | 1/2009 |

OTHER PUBLICATIONS

International Search Report for PCT/JP2015/080391 dated Dec. 1, 2015 [PCT/ISA/210].

* cited by examiner

*Primary Examiner* — John M Mauro
(74) *Attorney, Agent, or Firm* — Sughrue Mion, PLLC

(57) ABSTRACT

A polyvalent glycidyl compound is produced from a compound having one or more 2-alkenyl ether groups and two or more 2-alkenyl groups using a hydrogen peroxide aqueous solution as an oxidizing agent to oxidize the 2-alkenyl ether groups and the 2-alkenyl groups. A 2-alkenyl ether compound having two or more (un)substituted 2-alkenyl groups and one or more (un)substituted 2-alkenyl ether groups is oxidized using a hydrogen peroxide aqueous solution as an oxidizing agent in the presence of a tungsten compound and a quaternary ammonium salt as catalysts and of phosphoric acid as a co-catalyst, while controlling the pH of the reaction solution to 1.0-4.0 using an acid other than phosphoric acid. During the oxidation, the step of adding the hydrogen peroxide aqueous solution to the reaction solution and the step of adding the acid other than phosphoric acid thereto are alternately repeated at intervals two or more times.

12 Claims, No Drawings

PROCESS FOR PRODUCING POLYVALENT GLYCIDYL COMPOUND

CROSS REFERENCE TO RELATED APPLICATIONS

This application is a National Stage of International Application No. PCT/JP2015/080391, filed on Oct. 28, 2015 (which claims priority from Japanese Patent Application No. 2014-229965, filed on Nov. 12, 2014), the contents of which are incorporated herein by reference in their entirety.

TECHNICAL FIELD

The present invention relates to a method for producing a polyvalent glycidyl (epoxy) compound. More particularly, the present invention relates to a method for producing a polyvalent glycidyl compound that serves as a raw material of a curable resin composition having superior hardness, strength and heat resistance, in particular, suitable for the field of electronic materials.

BACKGROUND ART

Glycidyl (epoxy) compounds are used in numerous applications in such fields as coating material, civil engineering and electrical material due to their superior electrical characteristics, adhesiveness and heat resistance. In particular, aromatic glycidyl (epoxy) compounds such as bisphenol A diglycidyl ethers, bisphenol F diglycidyl ethers, phenol novolak epoxy resins or cresol novolak epoxy resins are widely used in combination with various curing agents due to their superior water resistance, adhesiveness, mechanical properties, heat resistance, electrical insulating properties and economic feasibility.

Glycidyl compounds are molecularly designed so as to coincide with target properties in order to improve the physical properties of resins containing the glycidyl compounds and curing agents. In the case of bisphenol A diglycidyl ethers, for example, the optical characteristics (transparency) of cured products and fluidity during curing is known to improve as a result of hydrogenating aromatic rings at phenol moieties of the basic skeleton to derive an aliphatic cyclohexane skeleton. In the case of phenol novolak epoxy resins, fluidity during curing can be changed or heat resistance or adhesiveness and the like of cured products can be controlled by adjusting the degree of polymerization or molecular weight distribution of the glycidyl compound.

The introduction of multiple functional groups into glycidyl compounds is known as a technique for improving characteristics, such as the heat resistance or adhesiveness of cured resins containing a glycidyl compound and curing agent. The number of crosslinking reaction sites between a glycidyl compound and curing agent can be increased by increasing the density of reactive functional groups in the resin (amount of functional group contained per molecule). Since the crosslink density per unit volume of the cured product increases, molecular micro-motion is controlled and resistance of the cured product to external effects is enhanced. As a result, heat resistance of the cured product is improved and properties, such as rigidity or adhesiveness can be imparted to the cured product.

A known technique for introducing multiple functional groups into a glycidyl compound comprises introducing two or more glycidyl groups into an aromatic ring skeleton of a glycidyl compound having an aromatic ring skeleton to increase crosslink density. For example, Patent Document 1 (Japanese Unexamined Patent Publication No. S63-142019) discloses that polyvalent glycidyl compounds, having a glycidyl group at the ortho position or para position relative to a glycidyl ether group bonded to a phenol site of a compound having bisphenol for the basic skeleton thereof, have superior adhesiveness to metal, low hygroscopicity and favorable mechanical characteristics. These compounds are synthesized by using a phenol, such as bisphenol F, for the starting raw material, subjecting the phenolic hydroxyl group to 2-alkenylation, and subjecting the ortho position or para position to 2-alkenylation by Claisen rearrangement of the resulting 2-alkenyl ether group, followed by glycidyl etherification using epichlorohydrin and oxidation (glycidylation) of the side chain 2-alkenyl group.

However, in the oxidation (glycidylation) reaction during the final stage of the process, since an amount of an organic peroxide, such as peracetic acid, performic acid, m-chloroperbenzoic acid or peroxyphthalic acid, or an inorganic peroxide, such as permolybdic acid, pervanadic acid or pertungstic acid, is required that is equal to or greater than the chemical equivalent with respect to the reactive site in the form of a 2-alkenyl group, there were cases in which it was difficult to remove residues of these oxidizing agents from the target product, or the oxidizing agents were expensive and the process thus lacked industrial applicability. In addition, since epichlorohydrin is used in the synthesis process, in the case of producing compounds having a large number of functional groups, the content of organic chlorine compounds in the product increases as the amount of used epichlorohydrin increases.

In order to avoid contamination by organic chlorine compounds, it is effective to use a method that does not use epichlorohydrin when synthesizing glycidyl (epoxy) compounds. For example, one possible method for synthesizing polyvalent diglycidyl compounds having an aromatic ring skeleton comprises 2-alkenylation of the ortho position or para position by Claisen rearrangement of a 2-alkenyl phenyl ether, 2-alkenyl etherification of the resulting phenolic hydroxyl group, and simultaneous oxidation (glycidylation) of 2-alkenyl ether groups and 2-alkenyl groups at the ortho position or para position thereof. According to this method, the amount of chlorine in a glycidyl compound can be significantly reduced in principle since epichlorohydrin is not used. However, simultaneous oxidation of 2-alkenyl ether groups and 2-alkenyl groups at the ortho position or para position thereof has heretofore been unknown since it is typically difficult to control the reaction due to differences in reactivity between these groups.

PRIOR ART DOCUMENTS

Patent Documents

[Patent Document 1] Japanese Unexamined Patent Publication No. S63-142019

DISCLOSURE OF THE INVENTION

Problems to be Solved by the Invention

An object of the present invention is to provide a method for safely producing a polyvalent glycidyl compound at high yield and high purity by oxidizing 2-alkenyl ether groups and 2-alkenyl groups of a compound having 2-alkenyl ether groups and 2-alkenyl groups in a molecule thereof using a hydrogen peroxide aqueous solution as an oxidizing agent.

Means for Solving the Problems

As a result of conducting extensive research and experiments to solve the aforementioned problems, the inventors of the present invention found that, when oxidizing a compound having two or more 2-alkenyl groups and one or more 2-alkenyl ether groups in a molecule thereof in the presence of catalysts in the form of a tungsten compound and a quaternary ammonium salt and a co-catalyst in the form of phosphoric acid by using a hydrogen peroxide aqueous solution as an oxidizing agent while controlling the pH of the reaction solution by using an acid other than phosphoric acid, alternately repeating addition of a hydrogen peroxide aqueous solution to the reaction solution and addition of an acid other than phosphoric acid for the adjustment of the pH of the reaction solution multiple times at a certain interval can safely produce a polyvalent glycidyl compound having three or more glycidyl groups in a molecule thereof at high yield and high purity, thereby leading to completion of the present invention.

Namely, the present invention is as indicated below.

[1] A method for producing a polyvalent glycidyl compound comprising: oxidizing a 2-alkenyl ether compound having two or more substituted or unsubstituted 2-alkenyl groups and one or more substituted or unsubstituted 2-alkenyl ether groups in a molecule thereof by using a hydrogen peroxide aqueous solution as an oxidizing agent in the presence of catalysts in the form of a tungsten compound and a quaternary ammonium salt and in the presence of a co-catalyst in the form of phosphoric acid while controlling the pH of the reaction solution to 1.0 to 4.0 by using an acid other than phosphoric acid, the method further comprising a step of alternately repeating a step of adding the hydrogen peroxide aqueous solution to the reaction solution and a step of adding the acid other than phosphoric acid multiple times at a certain interval.

[2] The method for producing a polyvalent glycidyl compound described in [1], wherein the step of adding the hydrogen peroxide aqueous solution and the step of adding the acid other than phosphoric acid in the repetition step are repeated 2 to 20 times during the reaction at an interval of 0.1 hour to 1 hour each time.

[3] The method for producing a polyvalent glycidyl compound described in either of [1] or [2], wherein the step of adding the aqueous hydroxide solution and the step of adding the acid other than phosphoric acid in the repetition step are repeated at least twice until the total amount of the hydrogen peroxide aqueous solution added to the reaction solution reaches 0.5 equivalents relative to the total amount of carbon-carbon double bond of the 2-alkenyl groups and 2-alkenyl ether groups of the 2-alkenyl ether compound.

[4] The method for producing a polyvalent glycidyl compound described in any of [1] to [3], wherein the step of adding the hydrogen peroxide aqueous solution to the reaction solution and the step of adding the acid other than phosphoric acid are carried out within a range such that the temperature of the reaction solution does not exceed 50° C.

[5] The method for producing a polyvalent glycidyl compound described in any of [1] to [4], wherein the 2-alkenyl ether compound contains an aromatic ring in a molecule thereof, and has one or more substituted or unsubstituted 2-alkenyl ether groups directly bonded to the aromatic ring and two or more substituted or unsubstituted 2-alkenyl groups directly bonded to the aromatic ring, and the substituted or unsubstituted 2-alkenyl groups are located at the ortho position or para position relative to the substituted or unsubstituted 2-alkenyl ether groups.

[6] The method for producing a polyvalent glycidyl compound described in any of [1] to [5], wherein the 2-alkenyl ether compound is a compound represented by formula (1):

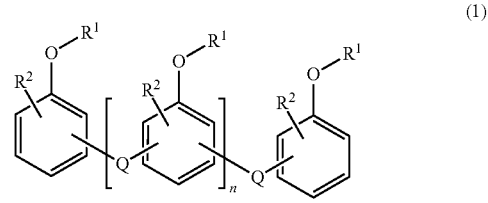

wherein $R^1$ and $R^2$ respectively and independently represent a group represented by the following formula (2), Q respectively and independently represents an alkylene group represented by the formula $-CR^2R^4-$, cycloalkylene group having 3 to 12 carbon atoms, arylene group composed of a single aromatic ring having 6 to 10 carbon atoms or arylene group obtained by linking two to three aromatic rings having 6 to 10 carbon atoms, divalent aliphatic condensed ring having 7 to 12 carbon atoms or divalent group comprising a combination thereof, $R^3$ and $R^4$ respectively and independently represent a hydrogen atom, alkyl group having 1 to 10 carbon atoms, alkenyl group having 2 to 10 carbon atoms, cycloalkyl group having 3 to 12 carbon atoms or aryl group having 6 to 10 carbon atoms, n represents an integer of 0 to 50, and $R^5$, $R^6$ and $R^7$ in formula (2) respectively and independently represent a hydrogen atom, alkyl group having 1 to 10 carbon atoms, cycloalkyl group having 3 to 12 carbon atoms or aryl group having 6 to 10 carbon atoms, or a compound having a naphthalene skeleton instead of the benzene skeleton of formula (1).

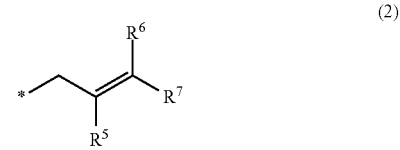

[7] The method for producing a polyvalent glycidyl compound described in [6], wherein the 2-alkenyl ether compound is a 2-alkenyl ether compound having the basic skeleton of any of bisphenol A, bisphenol F, phenol novolak, triphenylmethane phenol, biphenyl aralkyl phenol, phenyl aralkyl phenol, phenol of an unsubstituted tetrahydrodicyclopentadiene skeleton or phenol of an unsubstituted tetrahydrodicyclopentadiene skeleton having $-CH_2-$ bonded to both ends, and $R^2$ is located at the ortho position or para position relative to $OR^1$.

[8] The method for producing a polyvalent glycidyl compound described in any of [1] to [7], wherein the tungsten compound is any of a mixture of sodium tungstate and tungstic acid, a mixture of sodium tungstate and a mineral acid or a mixture of tungstic acid and an alkaline compound.

[9] The method for producing a polyvalent glycidyl compound described in any of [1] to [8], wherein the total number of carbon atoms of substituents bonded to the nitrogen atom of the quaternary ammonium salt is 6 to 50.

[10] The method for producing a polyvalent glycidyl compound described in any of [1] to [9], wherein the acid other than phosphoric acid is at least one type of mineral acid selected from the group consisting of polyphosphoric acid, pyrophosphoric acid, sulfonic acid, nitric acid, sulfuric acid, hydrochloric acid and boric acid, or is at least one type of organic acid selected from the group consisting of benzenesulfonic acid, p-toluenesulfonic acid, methanesulfonic acid, trifluoromethanesulfonic acid and trifluoroacetic acid.

Effects of the Invention

According to the method for producing a polyvalent glycidyl compound of the present invention, production costs can be reduced since residue derived from the oxidizing agent can be easily removed from a target product and a hydrogen peroxide aqueous solution, which is inexpensive, can be used for the oxidizing agent. In addition, as a result of controlling the temperature of the reaction solution by alternately repeating multiple times at a certain interval the addition of the hydrogen peroxide aqueous solution and the addition of the acid other than phosphoric acid for the purpose of controlling pH while controlling the pH of the reaction solution to 1.0 to 4.0, the amount of hydrolyzates as by-products can be reduced, thereby making it possible to safely obtain a polyvalent glycidyl compound at high yield and high purity. Consequently, the present invention allows the efficient production of an industrially useful polyvalent glycidyl compound. In addition, since an organic chlorine compound is not used in the reaction step, this method can be applied to electronic devices requiring a high level of electrical reliability.

MODE FOR CARRYING OUT THE INVENTION

The following provides a detailed explanation of the present invention. The method for producing a polyvalent glycidyl compound of the present invention consists of oxidizing a 2-alkenyl ether compound having two or more substituted or unsubstituted 2-alkenyl groups and one or more substituted or unsubstituted 2-alkenyl ether groups in a molecule thereof by using a hydrogen peroxide aqueous solution as an oxidizing agent in the presence of catalysts in the form of a tungsten compound and a quaternary ammonium salt and a co-catalyst in the form of phosphoric acid while controlling the pH of the reaction solution to 1.0 to 4.0 by using an acid other than phosphoric acid. At this time, the step of adding the hydrogen peroxide aqueous solution to the reaction solution and the step of adding the acid other than phosphoric acid are alternately repeated multiple times at a certain interval. Although the details thereof will be subsequently described, in the present invention, a polyvalent glycidyl compound having three or more glycidyl groups can be produced by oxidizing (glycidylating) the carbon-carbon double bonds of 2-alkenyl groups and 2-alkenyl ether groups present within a molecule. In the present description, "glycidyl group" includes substituted or unsubstituted glycidyl groups and substituted or unsubstituted glycidyl ether groups having a glycidyl skeleton. For example, "three or more glycidyl groups" means that the total number of substituted or unsubstituted glycidyl groups and substituted or unsubstituted glycidyl ether groups is three or more. In the present description, a "2-alkenyl ether group" refers to a 2-alkenyloxy group.

Although there are no particular limitations on the reaction substrate used in the oxidation reaction in the present invention provided it is a 2-alkenyl ether compound having two or more substituted or unsubstituted 2-alkenyl groups and one or more substituted or unsubstituted 2-alkenyl ether groups in a molecule thereof, a compound containing an aromatic ring, having one or more substituted or unsubstituted 2-alkenyl ether groups directly bonded to the aromatic ring and having two or more substituted or unsubstituted 2-alkenyl groups directly bonded to the aromatic ring, wherein the substituted or unsubstituted 2-alkenyl groups are located at the ortho position or para position relative to the substituted or unsubstituted 2-alkenyl ether groups, is preferable from the viewpoint of being relatively easily available. For example, a preferable example of a 2-alkenyl ether compound is represented by formula (1) indicated below.

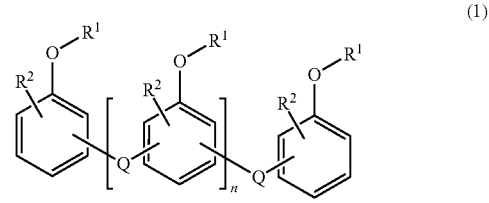

(1)

In the above formula, $R^1$ and $R^2$ respectively and independently represent a group represented by the following formula (2), Q respectively and independently represents an alkylene group represented by the formula $CR^3R^4$—, cycloalkylene group having 3 to 12 carbon atoms, arylene group composed of a single aromatic ring having 6 to 10 carbon atoms or arylene group obtained by linking two to three aromatic rings having 6 to 10 carbon atoms (for example, the arylene group obtained by linking two aromatic rings includes an arylene group having a biphenyl skeleton, and the arylene group obtained by linking three aromatic rings includes an arylene group having a triphenyl skeleton), divalent aliphatic condensed ring having 7 to 12 carbon atoms or a divalent group comprising a combination thereof, $R^3$ and $R^4$ respectively and independently represent a hydrogen atom, alkyl group having 1 to 10 carbon atoms, alkenyl group having 2 to 10 carbon atoms, cycloalkyl group having 3 to 12 carbon atoms or aryl group having 6 to 10 carbon atoms, n represents an integer of 0 to 50, and $R^5$, $R^6$ and $R^7$ in formula (2) respectively and independently represent a hydrogen atom, alkyl group having 1 to 10 carbon atoms, cycloalkyl group having 3 to 12 carbon atoms, or aryl group having 6 to 10 carbon atoms. Asterisks (*) in formula (2) indicate a binding site with an oxygen atom or a carbon atom that composes the aromatic ring.

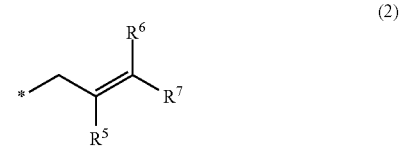

(2)

Preferable examples of $R^1$ and $R^2$ of the specific 2-alkenyl ether compound represented by the aforementioned formula (1) include groups represented by formula (2) in which $R^5$ to $R^7$ are all hydrogen atoms. Preferable examples of Q include alkylene groups represented by the formula —CR$^3$R$^4$— in which R$^3$ and R$^4$ respectively and independently represent a hydrogen atom, alkyl group having 1 to 10 carbon atoms, phenyl group or naphthyl group. Preferable examples of cycloalkylene groups having 3 to 12 carbon atoms include cyclohexylidene groups. Preferable examples of arylene groups composed of a single aromatic ring having 6 to 10 carbon atoms and arylene groups obtained by linking two to three aromatic rings having 6 to 10 carbon atoms include a phenylene group and biphenyldiyl group. Preferable examples of divalent alicyclic condensed rings having 7 to 12 carbon atoms include divalent tetrahydrodicyclopentadiene rings. Preferable examples of divalent groups obtained by combining these groups include a —CH$_2$-Ph-Ph-CH$_2$— group (in the present description, Ph refers to an unsubstituted benzene ring) and —CH$_2$-Ph-CH$_2$— group. Specific preferable examples of these compounds include 2-alkenyl ether compounds having the basic skeleton of any of bisphenol A, bisphenol F, phenol novolak, triphenylmethane phenol, biphenyl aralkyl phenol having, for example, a —CH$_2$-Ph-Ph-CH$_2$— skeleton, phenyl aralkyl phenol having, for example, a —CH$_2$-Ph-CH$_2$— skeleton, and phenol of an unsubstituted tetrahydrodicyclopentadiene skeleton or phenol of an unsubstituted tetrahydrodicyclopentadiene skeleton having —CH$_2$— bonded to both ends in which R$^2$ is located at the ortho position or para position relative to OR$^1$. In addition, examples of 2-alkenyl ether compounds other than 2-alkenyl ether compounds represented by the aforementioned formula (1) include compounds having a naphthalene skeleton instead of the benzene skeleton of formula (1), such as naphthalene novolak.

As an example thereof, a compound in which 2-alkenyl groups are located at the ortho position or para position of phenolic hydroxyl groups can be obtained by using a known phenol resin, such as bisphenol compounds including 4,4'-dihydroxydiphenyldimethylmethane (bisphenol A) and 4,4'-dihydroxydiphenylmethane (bisphenol F), or a novolak derived from phenol and formaldehyde, converting this to the corresponding 2-alkenyl ether compound, subjecting the 2-alkenyl ether compound to a Claisen rearrangement to derive the 2-alkenyl ether compound to a phenol compound. A compound represented by formula (1) can then be obtained by again converting this phenol compound to the corresponding 2-alkenyl ether compound.

The reaction through the Claisen rearrangement stage includes use of a commercially available phenol compound for the starting substance, 2-alkenyl etherification as indicated below, and subsequent conversion by rearrangement under heating conditions. A method comprising using a metal catalyst and an allyl Carboxylate as an allylation agent is known for a subsequent conversion step to a 2-alkenyl ether compound, for example, as described in U.S. Pat. No. 5,578,740. In this method, a phenol that has undergone 2-alkenylation of the ortho position is converted to an allyl ether compound having two or more 2-alkenyl groups in a molecule thereof by an allyl etherification reaction.

During 2-alkenyl etherification, the use of a 2-alkenyl chloride for the 2-alkenylation agent is preferably avoided in order to lower the chlorine content in the product 2-alkenyl ether compound. Although examples of 2-alkenylation agents include allyl acetate, allyl alcohol, allyl carbonate and allyl carbamate, industrially inexpensive allyl acetate and allyl alcohol are preferable. A method for converting to an allyl ether using a metal catalyst is disclosed in, for example, J. Muzart, et al., J. Organomet. Chem., 326, pp. C23-C28 (1987) as an example of 2-alkenylation of a phenolic hydroxyl group.

In the method for producing a polyvalent glycidyl compound of the present invention, the carbon-carbon double bonds of 2-alkenyl groups and 2-alkenyl ether groups of the reaction substrate in the form of the aforementioned 2-alkenyl ether compound are oxidized (glycidylated) by using a hydrogen peroxide aqueous solution as an oxidizing agent. Although there are no particular limitations on the concentration of the hydrogen peroxide aqueous solution, it is typically selected from a range of about 1% by mass to about 80% by mass and preferably from a range of about 20% by mass to about 60% by mass. Although the hydrogen peroxide aqueous solution is preferably used at a high concentration from the viewpoint of industrial productivity and from the viewpoint of operability during separation and/or costs, it is preferable from the viewpoints of economic feasibility and safety to not use an excessively high concentration and/or excessively large amount of the hydrogen peroxide aqueous solution.

The pH of the reaction solution changes when the hydrogen peroxide aqueous solution is added to the reaction solution. The inventors of the present invention focused on the finding that control of the pH of the reaction solution is extremely important for achieving the object of the present invention, and found that, in an embodiment of the present invention, the inclusion of a step of alternately repeating multiple times at a certain interval a step of adding a hydrogen peroxide aqueous solution to the reaction solution (referred to as the "first step") and a step of adding an acid other than phosphoric acid to control pH (referred to as the "second step") is extremely effective. More specifically, when defining the number of repetitions as n and focusing on an arbitrary kth repetition (2≤k≤n), the (k−1)th repetition of the second step is carried out after a time interval T1 following completion of the (k−1)th repetition of the first step, and the kth repetition of the first step is carried out after a time interval T2 following completion of the (k−1)th repetition of the second step. The session starting from the (k−1)th repetition of the first step to prior to the kth repetition of the first step is defined as a single sequential repetition step, and is repeated n times. Although the same conditions can be used for each of the first step, T1, second step and T2 in the repetition step repeated n times, different conditions can also be used.

The present reaction system is a biphasic system consisting of an organic phase based on an organic solvent or the 2-alkenyl ether compound itself and an aqueous phase based on the added hydrogen peroxide aqueous solution, and an emulsion-like system normally results accompanying stirring of the reaction solution. In the case of adding a hydrogen peroxide aqueous solution or an acid other than phosphoric acid to the reaction solution, the relative ratio of the aqueous phase in the reaction solution is low in an early stage of the reaction, and the true value of pH cannot be monitored with a pH analyzer that is directed to an aqueous solution as the measurement target. Consequently, the pH value of the reaction solution can be estimated from the monitoring value obtained by measuring pH after having sampled a portion of the solution and diluted by a factor of about 2 to 10 by using water to increase the water ratio thereof. According to the present invention, an excessive decrease in the pH of the reaction system can be prevented by providing an interval between addition of the hydrogen peroxide aqueous solution (oxidizing agent) and addition of the acid other than phosphoric acid (pH adjusting agent). In this manner, the pH of the reaction solution can be precisely controlled even in the early stage of the reaction when it is difficult to directly monitor the pH of the reaction solution.

For example, although the pH of the reaction solution following a single addition of a hydrogen peroxide aqueous solution and addition of an acid other than phosphoric acid is observed to apparently be about 5, the true pH value estimated from the value obtained by measuring an emulsion after diluting 10-fold is about 4.

In an embodiment of the present invention, although a hydrogen peroxide aqueous solution is initially added to a reaction solution charged with a substrate, catalyst and the like, the pH of the reaction solution at this stage is not outside the range of 1.0 to 4.0 since phosphoric acid is contained in the reaction solution as co-catalyst. In fact, prior to adding an acid other than phosphoric acid, the estimated pH value, as calculated from a measured value obtained by sampling a portion of the solution, diluting with water and then measuring the pH of the aqueous layer, is 4.0 or lower. Although the pH gradually lowers as a result of adding an acid other than phosphoric acid, the amount added is adjusted so that the pH does not drop lower than 1.0.

When the reaction reaches the stage at which the pH of the reaction solution can be directly measured with a pH analyzer, buffering action occurs due to the combined presence of hydrogen peroxide, phosphoric acid, an acid other than phosphoric acid (preferably, sulfuric acid) and the tungsten compound in the reaction solution. Once the reaction reaches this stage, a large change in the pH of the reaction solution does not occur even if the remaining hydrogen peroxide aqueous solution and acid other than phosphoric acid are added all at once.

In a preferred embodiment of the present invention, the aforementioned first step and second step are repeated multiple times, and for example, 2 to 20 times during the reaction at an interval between the two steps of 0.1 hour to 1 hour each time. As a more specific example thereof, the hydrogen peroxide aqueous solution is initially added such that the amount of the hydrogen peroxide aqueous solution added to the reaction solution is within the range of 0.05 equivalents to 0.3 equivalents relative to the total amount of carbon-carbon double bond of the 2-alkenyl groups and 2-alkenyl ether groups of the 2-alkenyl ether compound (first step), and after continuing the reaction for 0.1 hour to 1 hour (corresponding to the aforementioned T1) following completion of addition, the acid other than phosphoric acid is added within a range such that the pH of the reaction solution is held within the range of 1.0 to 4.0 (within a range of, for example, 5% by mass to 30% by mass of the total added amount) as an initial second step, and the reaction is continued for 0.1 hour to 1 hour following completion of addition (corresponding to the aforementioned T2). Namely, a time interval of 0.1 hour to 1 hour is provided following completion of the initial first step until the start of the second step, and a time interval of 0.1 hour to 1 hour is provided following completion of the initial second step to the start of the second first step. As a result of employing these steps, sudden decreases in the pH of the reaction solution can be prevented and the residual accumulated amount of hydrogen peroxide can be adjusted. In the first step and the second step, addition is preferably carried out intermittently or continuously in small amounts while stirring the reaction solution, and addition is more preferably carried out over the course of 0.1 hour to 1.5 hours. Stirring of the reaction solution is also preferably continued between both steps (T1 and T2). The second addition of the hydrogen peroxide aqueous solution (first step) is then carried out within a range such that the total amount of a hydrogen peroxide aqueous solution added to the reaction solution (total amount of the first addition and second addition) is 0.1 equivalents to 0.5 equivalents relative to the total amount of carbon-carbon double bond of the 2-alkenyl groups and 2-alkenyl ether groups of the 2-alkenyl ether compound, and after continuing the reaction for 0.1 hour to 1 hour following completion of addition (corresponding to the aforementioned T1), the acid other than phosphoric acid is added as the second round of the second step within a range such that the pH of the reaction solution is held within the range of 1.0 to 4.0 (within a range of, for example, 5% by mass to 30% by mass of the total added amount), and the reaction continues for 0.1 hour to 1 hour following completion of addition (corresponding to the aforementioned T2).

Although the number of repetitions n is only required to be 2 or more, in consideration of such factors as reaction time, reaction efficiency or labor, n is preferably 3 to 20, n is more preferably 4 to 15 and n is even more preferably 5 to 10.

In a preferred embodiment of the present invention, the repetition step is carried out at least twice until the total amount of a hydrogen peroxide aqueous solution added to the reaction solution reaches 0.5 equivalents relative to the total amount of carbon-carbon double bond of the 2-alkenyl groups and 2-alkenyl ether groups of the 2-alkenyl ether compound. At this time, n is preferably 3 to 20. In another preferred embodiment, the repetition step is carried out at least twice until the total amount of a hydrogen peroxide aqueous solution added to the reaction solution reaches 0.4 equivalents relative to the total amount of carbon-carbon double bond of the 2-alkenyl groups and 2-alkenyl ether groups of the 2-alkenyl ether compound. At this time, n is preferably 4 to 15. In still another preferred embodiment, the repetition step is carried out at least twice until the total amount of a hydrogen peroxide aqueous solution added to the reaction solution reaches 0.3 equivalents relative to the total amount of carbon-carbon double bond of the 2-alkenyl groups and 2-alkenyl ether groups of the 2-alkenyl ether compound. At this time, n is preferably 5 to 10. As a result of alternately repeating the first and second steps multiple times to minimize the amount added per repetition, in comparison with the case of collectively carrying out both steps simultaneously, the pH of the reaction solution can be more easily controlled during the reaction (namely, fluctuations in pH can be reduced), rapid progression of the reaction and temperature rises in accompaniment thereto can be inhibited, and the oxidation reaction can be allowed to proceed safely and efficiently.

In the addition time of the hydrogen peroxide aqueous solution becomes longer (slower addition rate), the concentration of hydrogen peroxide in the reaction system may decrease, together with a decrease in efficiency of the oxidation reaction, hydrolysis may occur in competition therewith. Furthermore, since the reaction may proceed rapidly resulting in danger if a large amount of a hydrogen peroxide aqueous solution is added all at once to the reaction solution in an early stage of the reaction, the hydrogen peroxide aqueous solution is preferably added continuously or intermittently while confirming the concentration of the hydrogen peroxide aqueous solution as to whether the hydrogen peroxide aqueous solution is consumed in the reaction while stirring the reaction solution. The total added amount of a hydrogen peroxide aqueous solution is 1.0 equivalent to 5.0 equivalents, preferably 1.1 equivalents to 3.0 equivalents, and more preferably 1.2 equivalents to 2.0 equivalents relative to the total amount of carbon-carbon double bond of the 2-alkenyl groups and 2-alkenyl ether groups of the 2-alkenyl ether compound. If the total added amount is less than 1.0 equivalent, it is not theoretically possible to oxidize all of the carbon-carbon double bonds of the 2-alkenyl groups and 2-alkenyl ether groups. If the total added amount exceeds 5.0 equivalents, a large amount of reducing agent is required to quench the excess oxidizing agent, thereby increasing the complexity of the post-treatment step.

The reaction is preferably allowed to proceed following completion of the aforementioned repetition step. Addition of a hydrogen peroxide aqueous solution in an amount, equal to or greater than the balance amount of a hydrogen peroxide aqueous solution obtained by subtracting the amount of a hydrogen peroxide aqueous solution added in the repetition step from the amount of a hydrogen peroxide aqueous solution at which the total amount of carbon-carbon double bond of the 2-alkenyl groups and 2-alkenyl ether groups of the 2-alkenyl ether compound is 1.0 equivalent, and the subsequent reaction are preferably allowed to continue while stirring the reaction solution. At this stage, an acid other than phosphoric acid can be added as necessary in order to adjust the pH of the reaction solution. Addition of an acid other than phosphoric acid may be carried out without a certain time interval following addition of the hydrogen peroxide aqueous solution, or may be carried out simultaneous to addition of the hydrogen peroxide aqueous solution.

A magnetic stirrer or a stirrer equipped with stirring blades is preferably used for stirring during the reaction, including the aforementioned repetition step. The stirring speed is generally within the range of 100 rpm to 2000 rpm and preferably within the range of 300 rpm to 1500 rpm. The reaction solution is biphasic, consisting of an organic phase containing the reaction substrate in the form of the 2-alkenyl ether compound or the 2-alkenyl ether compound dissolved in an organic solvent, and an aqueous phase containing hydrogen peroxide, and the two phases are preferably stirred until an emulsion-like mixture is formed. As the oxidation reaction (glycidylation) of carbon-carbon double bonds of the 2-alkenyl groups and 2-alkenyl ether groups progresses, a glycidyl compound is formed resulting in an increase in the viscosity of the reaction solution. In order to prevent hydrolysis of the glycidyl groups of the intermediate product or final product in the form of the glycidyl compound as well as the by-production of gel-like substances attributable thereto, after allowing the reaction to continue within the range of 2 hours to 30 hours following completion of addition of the hydrogen peroxide aqueous solution, stirring and heating are preferably discontinued to terminate the oxidation reaction. If the reaction is terminated in less than 2 hours, a large amount of the reaction substrate in the form of the 2-alkenyl ether compound is contained and the yield of the target product tends to decrease. If the reaction is allowed to continue for longer than 30 hours, the hydrolysis product is mainly produced, and a gel-like substance may be formed, resulting in complicated post-treatment of the reaction solution, which tends to lower the yield of the target product.

Oxidation (glycidylation) using the hydrogen peroxide aqueous solution can be carried out in the presence of catalysts in the form of a tungsten compound and a quaternary ammonium salt and a co-catalyst in the form of phosphoric acid while controlling the pH of the reaction solution by using an acid other than phosphoric acid. Since these compounds are comparatively inexpensive, oxidation of carbon-carbon double bonds of the 2-alkenyl groups and 2-alkenyl ether groups of the 2-alkenyl ether compound by using hydrogen peroxide as an oxidizing agent can be carried out at low cost.

It is preferable that the tungsten compound used as catalyst be a compound that forms tungstate anions in water. Examples thereof include tungstic acid, tungsten trioxide, tungsten trisulfide, tungsten hexachloride, phosphotungstic acid, ammonium tungstate, potassium tungstate dihydrate and sodium tungstate dihydrate. Tungstic acid, tungsten trioxide, phosphotungstic acid and sodium tungstate dihydrate are preferable. These tungsten compounds may be used alone or two or more types may be used as a mixture.

The catalytic activity of these compounds that form tungstate anions in water is higher if counter cations are present at about 0.2 moles to about 0.8 moles per 1 mole of tungstate anions. An exemplary method for preparing such a tungsten composition comprises mixing tungstic acid with an alkaline metal salt of tungstic acid so that tungstate anions and counter cations satisfy the aforementioned ratio, or mixing tungstic acid with an alkaline compound (such as a hydroxide or carbonate of an alkaline metal or alkaline earth metal) or combining an alkaline metal salt or alkaline earth metal salt of tungstic acid with an acidic compound such as a mineral acid, for example, phosphoric acid or sulfuric acid. Specific preferable examples thereof include a mixture of sodium tungstate and tungstic acid, a mixture of sodium tungstate and a mineral acid, and a mixture of tungstic acid and an alkaline compound.

The amount of tungsten compound catalyst used in terms of tungsten atoms is selected from the range of about 0.0001 mol % to about 20 mol % and preferably about 0.01 mol % to 20 mol % based on the total amount of carbon-carbon double bond of the 2-alkenyl groups and 2-alkenyl ether groups of the reaction substrate in the form of the 2-alkenyl ether compound.

The quaternary ammonium salt used as catalyst is preferably a quaternary organic ammonium salt in which the total number of carbon atoms of substituents bonded to the nitrogen atom thereof is 6 to 50 and preferably 10 to 40, due to the high oxidation (glycidylation) activity thereof.

Examples of quaternary ammonium salts include chlorides such as trioctyl methyl ammonium chloride, trioctyl ethyl ammonium chloride, dilauryl dimethyl ammonium chloride, lauryl trimethyl ammonium chloride, stearyl trimethyl ammonium chloride, lauryl dimethyl benzyl ammonium chloride, tricapryl methyl ammonium chloride, didecyl dimethyl ammonium chloride, tetrabutyl ammonium chloride, benzyl trimethyl ammonium chloride or benzyl triethyl ammonium chloride; bromides such as trioctyl methyl ammonium bromide, trioctyl ethyl ammonium bromide, dilauryl dimethyl ammonium bromide, lauryl trimethyl ammonium bromide, stearyl trimethyl ammonium bromide, lauryl dimethyl benzyl ammonium bromide, tricapryl methyl ammonium bromide, didecyl dimethyl ammonium bromide, tetrabutyl ammonium bromide, benzyl trimethyl ammonium bromide or benzyl triethyl ammonium bromide; iodides such as trioctyl methyl ammonium iodide, trioctyl ethyl ammonium iodide, dilauryl dimethyl ammonium iodide, lauryl trimethyl ammonium iodide, stearyl trimethyl ammonium iodide, lauryl dimethyl benzyl ammonium iodide, tricapryl methyl ammonium iodide, didecyl dimethyl ammonium iodide, tetrabutyl ammonium iodide, benzyl trimethyl ammonium iodide or benzyl triethyl ammonium iodide; hydrogen phosphates such as trioctyl methyl ammonium hydrogen phosphate, trioctyl ethyl ammonium hydrogen phosphate, dilauryl dimethyl ammonium hydrogen phosphate, lauryl trimethyl ammonium hydrogen phosphate, stearyl trimethyl ammonium hydrogen phosphate, lauryl dimethyl benzyl ammonium hydrogen phosphate, tricapryl methyl ammonium hydrogen phosphate, didecyl dimethyl ammonium hydrogen phosphate, tetrabutyl ammonium hydrogen phosphate, benzyl trimethyl ammonium hydrogen phosphate or benzyl triethyl ammonium hydrogen phosphate; and hydrogen sulfates such as trioctyl methyl ammonium hydrogen sulfate, trioctyl ethyl ammonium hydrogen sulfate, dilauryl dimethyl ammonium hydrogen sulfate, lauryl trimethyl ammonium hydrogen sulfate, stearyl trimethyl ammonium hydrogen sulfate, lauryl dimethyl benzyl ammonium hydrogen sulfate, tricapryl methyl ammonium hydrogen sulfate, didecyl dimethyl ammonium hydrogen sulfate, tetrabutyl ammonium hydrogen sulfate, benzyl trimethyl ammonium hydrogen sulfate or benzyl triethyl ammonium hydrogen sulfate.

These quaternary ammonium salts may be used alone or two or more types may be used as a mixture. The amount used thereof is preferably selected from the range of about 0.0001 mol % to about 10 mol % and more preferably selected from the range of about 0.01 mol % to about 10 mol % based on the total amount of carbon-carbon double bond of the 2-alkenyl groups and 2-alkenyl ether groups of the reaction substrate in the form of the 2-alkenyl ether compound.

In the case of using a phase transfer catalyst having a chloride ion, bromide ion or iodide ion for the counter anion as a quaternary ammonium salt, the content of halide in the product increases. A quaternary ammonium salt remover disclosed in, for example, Japanese Unexamined Patent Publication No. 2010-70480, can be used to reduce the level of impurities derived from halogens in the product. Although it is possible to carry out the oxidation reaction by using a halogen-based quaternary ammonium salt, the procedure may be complicated since a step of removing the quaternary ammonium salt is required.

A co-catalyst in the form of phosphoric acid is used in the method for producing a polyvalent glycidyl compound of the present invention. Phosphoric acid generates an active species by coordinating the oxygen atoms thereof to the metal center of a tungsten which is the catalyst metal. In addition, the pH of the reaction solution is controlled to 1.0 to 4.0 by combining with the use of an acid other than phosphoric acid. The pH of the reaction solution is preferably 1.2 to 3.8 and more preferably 1.4 to 3.7. If the pH of the reaction solution is higher than 4.0, productivity decreases due to a decrease in the reaction rate, while if the pH of the reaction solution is lower than 1.0, hydrolysis of the glycidyl group tends to proceed, resulting in a reduction in yield. Moreover, in the case the pH of the reaction solution is lower than 1.0, generation of the heat of reaction would be considerable, which is thought to be due to the rapid formation of the catalyst active species, and the internal temperature of the reaction solution would rise gradually due to the heat of reaction even without heating, thereby possibly resulting in thermal runaway. The amount of phosphoric acid used is preferably selected from the range of about 0.1 mol % to about 10 mol % and more preferably selected from the range of about 1 mol % to about 10 mol % based on the total. amount of carbon-carbon double bond of the 2-alkenyl groups and 2-alkenyl ether groups of the reaction substrate in the form of the 2-alkenyl ether compound.

Any mineral acid or organic acid can be used for the acid other than phosphoric acid. Examples of mineral acids include polyphosphoric acid, pyrophosphoric acid, sulfonic acid, nitric acid, sulfuric acid, hydrochloric acid and boric acid. Examples of organic acids include benzenesulfonic acid, p-toluenesulfonic acid, methanesulfonic acid, trifluoromethanesulfonic acid and trifluoroacetic acid. The amount used thereof is preferably selected from the range of about 0.1 mol % to about 10 mol % and more preferably selected form the range of about 1 mol % to about 10 mol % based on the total amount of carbon-carbon double bond of the 2-alkenyl-groups and 2-alkenyl ether groups of the reaction substrate in the form of the 2-alkenyl ether compound. Among these acids, sulfuric acid is preferable since it has considerable buffering effects and makes easy to maintain the pH within the range of 1.0 to 4.0.

In the glycidylation reaction, the glycidylation reaction of the reaction substrate in the form of the 2-alkenyl ether compound can be allowed to proceed by mixing the hydrogen peroxide aqueous solution and the aforementioned catalysts either without using an organic solvent or using an organic solvent as necessary. In the case of using a solvent, since the reaction rate may decrease and undesirable reactions such as hydrolysis reactions may proceed more easily depending on the solvent, it is necessary to select an appropriate solvent. In the case that the reaction substrate in the form of the 2-alkenyl ether compound has excessively high viscosity or is a solid, the minimum required amount of organic solvent may be used. Preferable organic solvents that can be used include aromatic hydrocarbons, aliphatic hydrocarbons and alicyclic hydrocarbons such as toluene, xylene, hexane, octane or cyclohexane. Using at the minimal required concentration is advantageous in terms of production cost and the like. The amount of organic solvent used is preferably about 300 parts by mass or less and more preferably about 100 parts by mass or less based on 100 parts by mass of the 2-alkenyl ether compound.

In addition, in the oxidation (glycidylation) reaction, when considering safely carrying out production on an industrial scale, it is preferable that the catalysts and substrate be initially charged into the reactor followed by gradually adding the hydrogen peroxide aqueous solution while confirming whether it is consumed in the reaction while holding the reaction temperature at a constant temperature as much as possible. The use of such a method makes it possible to reduce the accumulated amount of hydrogen peroxide and minimize rises in pressure even if oxygen gas is generated due to abnormal degradation of hydrogen peroxide in the reactor.

Since side reactions increase if the reaction temperature is excessively high while the consumption rate of hydrogen peroxide decreases causing it to accumulate in the reaction solution if the reaction temperature is excessively low, the reaction temperature is preferably controlled in the range of about 20° C. or higher and about 70° C. or lower, more preferably about 25° C. or higher and about 60° C. or lower, and even more preferably about 0° C. or higher and about 50° C. or lower. Each of the reactions of the repetition step consisting of the first and second steps as well as those following completion of the repetition step are preferably carried out within the aforementioned temperature ranges. If the reaction temperature is set higher than 70° C., there is increased susceptibility to the occurrence of thermal runaway and the thermal decomposition reaction of the added hydrogen peroxide competes with the oxidation reaction resulting in the generation of combustion-supporting oxygen gas. In a preferred embodiment, the temperature of the reaction solution in the first and second steps is within a range that does not exceed 50° C.

Following completion of the reaction, although there are cases in which there is hardly any difference in specific gravity between the aqueous phase and organic phase, in such cases, the two layers can be separated without using an organic extraction solvent by mixing the aqueous layer with a saturated aqueous solution of an inorganic compound to create a difference in specific gravity with the organic layer. Since the specific gravity of the tungsten compound is particularly high, in order to cause the aqueous layer to migrate to the lower layer, the tungsten compound may be used in an amount that exceeds the aforementioned required amount used as catalyst. In this case, the tungsten compound is preferably recycled from the aqueous layer to enhance utilization efficiency of the tungsten compound.

On the other hand, there are cases in which the specific gravity of the organic layer may be close to 1.2 depending on the substrate. In such cases, the aqueous layer can be made to migrate to the upper layer and the organic layer can be made to migrate to the lower layer by additionally adding water to make the specific gravity of the aqueous layer to approach 1. In addition, an organic solvent such as toluene, cyclohexane, hexane, or methylene chloride can be used to extract the reaction solution, and the optimum separation method can be selected corresponding to the situation.

After having concentrated the organic layer separated from the aqueous layer in this manner, the resulting polyvalent glycidyl compound can be obtained by a conventional method, such as distillation, chromatographic separation, recrystallization or sublimation.

EXAMPLES

Although the following provides a detailed explanation of the present invention through examples thereof, the present invention is not limited to the following examples.

Synthesis Example 1: Synthesis of Substrate (4,4'-(dimethylmethylene)bis[2-(2-propenyl)phenyl diallyl ether])

A solution containing 1380 g (10.0 mol) of potassium carbonate (Nippon Soda Co., Ltd.) dissolved in 1250 g of pure water, 800 g (2.62 mol) of 4,4'-(dimethylmethylene) bis[2-(2-propenyl)phenol] represented by formula (3) (Daiwa Fine Chemicals Co., Ltd.) and 520 g (5.00 mol, solid) of sodium carbonate (Kanto Chemical Co., Ltd.) were charged into a 5 L 3-neck round bottom flask followed by replacing the air inside the reaction vessel with nitrogen gas and heating to 85° C. Under the flow of nitrogen gas, 2200 g (21.9 mol) of allyl acetate (Showa Denko 26.2 g (100 mmol) of triphenylphosphine (Hokko Chemical Industry Co., Ltd.) and 846 mg (0.200 mmol, as Pd atoms) of 50% aqueous 5% Pd/C-STD type (N.E. Chemcat Corp.) were added, and after raising the temperature to 105° C. and allowing to react for 4 hours in a nitrogen gas atmosphere, 220 g (2.19 mol) of allyl acetate were additionally added followed by continuing to heat for 12 hours. Following completion of the reaction and after allowing the reaction system to cool to room temperature, pure water was added until all of the precipitated salt dissolved to separate the reaction solution. The organic phase was separated followed by distilling off the organic solvent (70° C., 50 mmHg, 2 hours). After adding pure water (2000 g), 2000 g of toluene were added, and after confirming that a white sediment no longer precipitated while holding the temperature at 80° C. or higher, Pd/C was recovered by filtration. (using 1 micron membrane filter (KST-142-JA filter manufactured by Advantech Co., Ltd.) under pressure (0.3 MPa)). This filter residue was washed with 1000 g of toluene together with separating the aqueous layer. The organic layer was washed twice with 2000 g of pure water at 50° C. and the aqueous layer was confirmed to be neutral. After separating the organic layer, the organic layer was concentrated under reduced pressure to obtain a brown liquid having for the main component thereof 4,4'-(dimethylmethylene)bis[2-(2-propenyl)phenyl diallyl ether] represented by formula (4) (936 g, 2.41 mmol, yield: 92.0%). As a result of measuring this brown liquid by $^1$H-NMR, it was confirmed to contain the compound represented by formula (4) as the main component thereof. Measurement data assigned to the compound represented by formula (4) is as shown below.

$^1$H-NMR {400 MHz, CDCl$_3$, 27° C.}, δ1.66 (6H, s, CH$_3$) δ3.39 (4H, d, PhC$\underline{H}_2$CH=CH$_2$), δ4.95-5.55 (4H, m, PhCH$_2$CH=C$\underline{H}_2$), δ5.25 d, PhOCH$_2$CH=CH$\underline{H}$), δ5.42 (2H, d, PhOCH$_2$CH=CH$\underline{H}$), δ5.25 (4H, m, PhOCH$_2$C$\underline{H}$=CH$_2$, PhCH$_2$C$\underline{H}$=CH$_2$), δ6.73 (d, 2H, aromatic), δ6.90-7.08 (m, 2H, aromatic), δ7.13-7.40 (2H, m, aromatic).

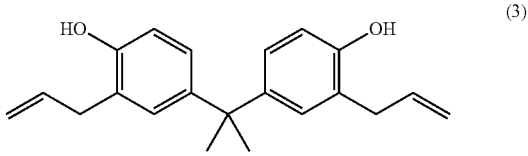

(3)

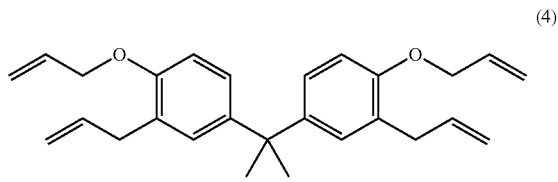

(4)

Example 1: Synthesis of 2,2-bis(3-glycidyl-4-glycidyloxy)propane

In a 2 L three-neck round bottom flask, 188 g (484 mmol) of 4,4'-(dimethylmethylene)bis[2-(2-propenyl)phenyl allyl ether] obtained in the aforementioned Synthesis Example 1, 12.8 g (38.7 mmol) of sodium tungstate dihydrate (Nippon Inorganic Colour & Chemical Co., Ltd.), 15.2 g (155 mmol) of phosphoric acid (Wako Pure Chemical Industries, Ltd.) and 40.9 g (87.2 mmol) of methyl trioctyl ammonium hydrogen sulfate (MTOAHS, Asahi Chemical Kogyo Co., Ltd.) were placed and dissolved in 180 g of toluene (Junsei Chemical Co., Ltd.). After raising the temperature to 40° C., 19 g (196 mmol) of a 35% by mass hydrogen peroxide aqueous solution (Ryoko Chemical Co., Ltd.) were added followed by stirring for 20 minutes, adding 1.9 g (6.71 mmol) of 35% dilute sulfuric acid (used after adjusting to 35% by mass by diluting concentrated sulfuric acid. (Wako Pure Chemical Industries, Ltd.) with pure water), and stirring for 20 minutes. This hydrogen peroxide aqueous solution addition step and sulfuric acid addition step were alternately carried out five times each over a total of 3 hours and 20 minutes. After confirming that the pH had reached 1.4, a hydrogen peroxide aqueous solution was added over the course of 2 hours so that the total added amount was 282 g (2.91 mol). Following completion of dropping, stirring was continued for 16 hours at 40° C. (stirring speed: 400 rpm). The pH of the reaction solution at 1 hour after completion of addition was 1.1, and the pH of the reaction solution after another 6 hours was 1.8. Following completion of the reaction, after allowing the reaction solution to cool to room temperature, 300 g of toluene were added to separate the reaction solution. The organic layer was separated and washed by adding 1220 g of aqueous sodium sulfite solution (10% by Mass, Wako Pure Chemical Industries, Ltd.) to reduce residual hydrogen peroxide. The aqueous layer was then removed followed by washing the organic layer again by adding 500 g of pure water. The organic layer was isolated followed by distilling off the organic solvent (toluene) to obtain 201 g of product in which the relative content of epoxy compound (EP ratio theoretical epoxy equivalent/measured epoxy equivalent)×100) was 94.0% (445 mmol, epoxy equivalent: 120, yield 92.0%). Yield was calculated as (acquired amount of mixture containing target epoxy compound after the aforementioned post-treatment/amount of substance obtained when oxidation reaction proceeds at reaction rate of 100%)×100. The epoxy equivalent of the product is close to the theoretical epoxy equivalent of the compound represented by formula (5), thereby suggesting that the product contains almost no hydrolysate of glycidyl group. As a result of measuring this product by $^1$H-NMR, the product was confirmed to contain the compound represented by formula (5) as the main component thereof. Measurement data assigned to the compound represented by formula (5) is as shown below.

$^1$H-NMR {400 MHz, CDCl$_3$, 27° C.}, δ1.64 (6H, s, CH$_3$), δ2.54 (2H, m, PhCH$_2$CHCH$_H$HO), δ2.7-2.8 (6H, m, PhCH$_2$CHCHHO, PhCH$_2$CHCH$_H$HO), δ2.90 (4H, m, PhOCH$_2$CHCH$_2$O), δ3.17 (2H, m, PhOCH$_2$CHCH$_H$HO), δ3.35 (2H, m, PhOCH$_2$CHCH$_H$HO), δ3.95 (2H, m, PhCH$_2$CHCH$_2$O), δ4.24 (2H, dd, PhOCH$_2$CHCH$_2$O), δ6.74 (d, 2H, aromatic), δ7.02-7.05 (m, 4H, aromatic).

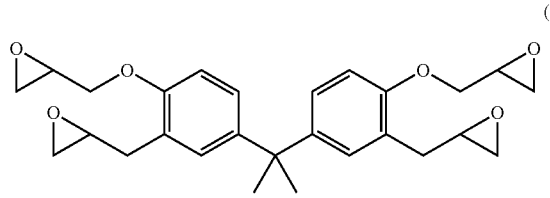

(5)

Synthesis Example 2: Synthesis of Substrate (Phenol Novolak Allyl Ether Having Allyl Group at Ortho Position or Para Position (abbreviated as BRG-556-AL2))

A solution containing 258.2 g (1.87 mol) of potassium carbonate (Nippon Soda Co., Ltd.) dissolved in 155.6 g of pure water, 100 g of phenol novolak represented by formula (6) (Shonol® BRG-556, o=2 to 7, mean value: 5.1, Showa Denko K.K.) and 65.6 g (0.62 mmol, solid) of sodium carbonate (Kanto Chemical Co., Ltd.) were charged into a 1 L 3-neck flask followed by replacing the air inside the reaction vessel with nitrogen gas and heating to 85° C. Under the flow of nitrogen gas, 168.3 g (1.68 mol) of allyl acetate (Showa Denko K.K.), 4.90 g (18.7 mmol) of triphenylphosphine (Hokko Chemical Industry Co., Ltd.) and 1.59 g (0.374 mmol, as Pd atoms) of 50% aqueous 5% Pd/C-STD type (N.E. Chemcat Corp.) were added, and after raising the temperature to 105° C. and allowing to react for 4 hours in a nitrogen gas atmosphere, 18.7 g (187 mmol) of allyl acetate were additionally added followed by continuing to heat for 12 hours. The reaction solution subsequently separated into an organic phase and aqueous phase as a result of discontinuing stirring and allowing to stand undisturbed. After adding pure water (200 g) until the precipitated salt dissolved, 200 g of toluene were added, and after confirming that a white sediment no longer precipitated while holding the temperature at 80° C. or higher, Pd/C was recovered by filtration (using 1 micron membrane filter (KST-142-JA filter manufactured by Advantech Co., Ltd.) under pressure (0.3 MPa)). This filter residue was washed with 100 g of toluene together with separating the aqueous layer. The organic layer was washed twice with 200 g of pure water at 50° C. and the aqueous layer was confirmed to be neutral. After separating the organic layer, the organic layer was concentrated under reduced pressure to obtain a brown oily substance (137 g, quantitative). As a result of measuring this brown oily substance by $^1$H-NMR, it was confirmed to contain the phenol novolak allyl ether (abbreviated as BRG-556-AL) represented by formula (7) as the main component thereof. Measurement data assigned to the compound represented by formula (7) is as shown below.

$^1$H-NMR (400 MHz, CDCl$_3$, 27° C.), δ3.6-4.0 (4H, m, PhCH$_2$Ph), δ4.4-4.8 (2H, m, CH$_2$CH—CH$_2$), δ5.1-5.3 (1H, m, CH$_2$CH=CHH), δ5.3-5.5 (1H, m, CH$_2$CH=CHH), δ5.8-6.2 (1H, m, CH$_2$CHCH$_2$), δ6.6-7.3 (12H, m, aromatic).

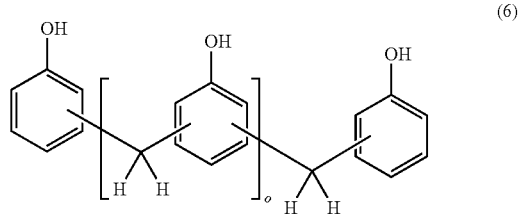

(6)

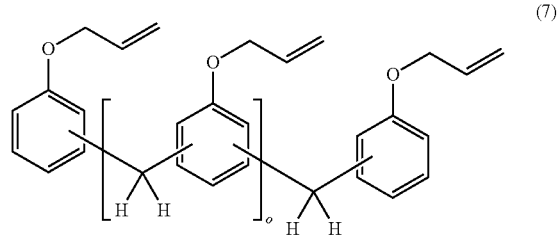

(7)

In a 300 recovery flask, 100 g of the phenol novolak allyl ether obtained in the aforementioned synthesis were placed together with a magnetic stirrer followed by heating at 190° C. in a nitrogen gas atmosphere. Three hours later, the reaction solution was cooled to obtain a black solid (98 g, quantitative). As a result of measuring this black solid by $^1$H-NMR, it was confirmed to contain the allyl-substituted phenol novolak (abbreviated as BRG-556-CL) represented by formula (8) as the main component thereof. Measurement data assigned to the compound represented by formula (8) is as shown below.

$^1$H-NMR {400 MHz, CDCl$_3$, 27° C.}, δ3.2-3.4 (2H, m, CH$_2$CH=CH$_2$), δ3.6-4.0 (5H, m, PhCH$_2$Ph, OH), δ4.6-5.0 (1H, m, CH$_2$CH=CHH), δ5.0-5.3 (1H, m, CH$_2$CH=CHH), δ5.8-6.1 (1H, m, CH$_2$CH=CH$_2$), δ6.6-7.2 (12H, m, aromatic).

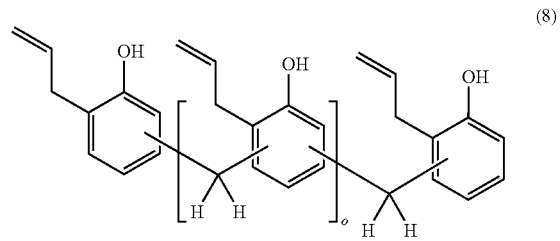

(8)

A phenol novolak allyl ether having allyl groups at the ortho position or para position was synthesized by using allyl acetate in the same manner as Synthesis Example 1 with the exception of changing 4,4'-(dimethylmethylene)bis[2-(2-propenyl)phenol] in Synthesis Example 1 to the allyl-substituted phenol novolak (BRG-556-CL) obtained in the aforementioned synthesis to obtain a brown oily substance (yield: 92%). As a result of measuring this brown oily substance by $^1$H-NMR, it was confirmed to contain the phenol novolak allyl ether having allyl groups at the ortho position or para position (abbreviated as BRO-556-AL2) represented by formula (9) as the main component thereof. Measurement data assigned to the compound represented by formula (9) is as shown below.

$^1$H-NMR {400 MHz, CDCl$_2$, 27° C.}, δ3.4-4.0 (4H, m, PhOC$\underline{H}_2$CH=CH$_2$, PhC$\underline{H}_2$CH=CH$_2$), δ4.3-4.9 (4H, m, PhCH$_2$Ph), δ5.2-5.3 (4H, m, PhOCH$_2$CHC=$\underline{HH}$, PhCH$_2$CH=C$\underline{HH}$), δ5.3-5.5 (2H, m, PhOCH$_7$CHC=$\underline{HH}$, PhCH$_2$CH=C$\underline{HH}$), δ5.8-6.2 (1H, m, PhOCH$_2$C$\underline{H}$C=H$_2$, PhCH$_2$C$\underline{H}$=CH$_2$), δ6.5-7.3 (12H, m, aromatic).

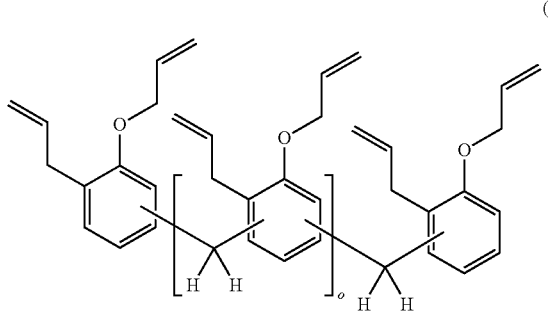

(9)

Example 2: Synthesis of Phenol Novolak Polyvalent Glycidyl Compound

In a 200 mL three-neck round bottom flask, 100 g of the phenol novolak allyl ether having allyl groups at the ortho position or para position (BRG-556-AL2) obtained in the aforementioned. Synthesis Example 2 containing about 534 mmol as the total amount of carbon-carbon double bond of 2-alkenyl groups and 2-alkenyl ether groups (calculated based on the molecular weight of the repeating unit of formula (9)), 7.05 g (21.4 mmol) of sodium tungstate dihydrate, 4.19 g (42.8 mmol) of phosphoric acid and 22.6 g (48.1 mmol) of MTOAHS were placed and dissolved in 150 g of toluene (Junsei Chemical Co., Ltd.). After raising the temperature to 40° C., 10.0 g (100 mmol) of a 35% by mass hydrogen peroxide aqueous solution were added followed by stirring for 20 minutes, adding 2 g (7.14 mmol) of 35% by mass dilute sulfuric acid, and stirring for 20 minutes. This hydrogen peroxide aqueous solution addition step and sulfuric acid addition step were alternately carried out four times each over a total of 2 hours and 40 minutes. After confirming that the pH had reached 1.8, a hydrogen peroxide aqueous solution was added over the course of 1 hour so that the total added amount was 156 g (1.60 mol). Following completion of dropping, stirring was continued for 16 hours at 40° C. (stirring speed: 400 rpm). The pH of the reaction solution at 1 hour after completion of addition was 1.2, and the pH of the reaction solution after another 2 hours was 2.0. Following completion of the reaction, after allowing the reaction solution to cool to room temperature, 150 g of toluene were added to separate the reaction solution. The organic layer was separated and washed by adding 130 g of an aqueous sodium sulfite solution (10% by mass) to reduce residual hydrogen peroxide. The aqueous layer was then removed followed by washing the organic layer again by adding 150 g of pure water. The organic layer was isolated followed by distilling off the organic solvent (toluene). Obtained were 93 g of a brown, highly viscous oily substance in which the epoxy equivalent was 140.1 and the EP ratio was 78.2% (425 mmol, yield: 79.4%). As a result of measuring this brown, highly viscous oily substance by $^1$H-NMR, it was confirmed to contain the phenol novolak polyvalent glycidyl compound represented by formula (10) as the main component thereof. Measurement data assigned to the compound represented by formula (10) is as shown below.

$^1$H-NMR {400 MHz, CDCl$_2$, 27° C.}, δ2.5-2.8 (2H, m, POC$\underline{H}_2$CHCH$_2$O) δ2.8-3.0 (4H, m, PhC$\underline{H}_2$CHCH$_2$O, PhCH$_2$CHC$\underline{H}_2$O), δ3.1-3.4 (2H, m, PhOCH$_2$CHCH$_2$O), δ3.6-4.0 (6H, m, PhCH$_2$Ph, PhOCH$_2$C$\underline{H}$CH$_2$O, PhCH$_2$C$\underline{H}$CH$_2$O), δ6.6-7.2 (12H, m, aromatic).

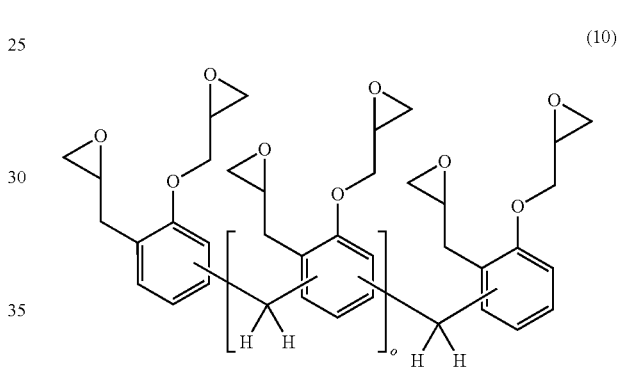

(10)

Comparative Example 1

A glycidylation reaction was carried out in the same manner as Example 1 with the exception of adding the reactants all at once (total amount of a hydrogen peroxide aqueous solution added: 282 g (2.91 mol), amount of sulfuric acid added: 9.5 g (33.6 mmol), reaction time: 18 hours) instead of alternately adding the hydrogen peroxide aqueous solution and sulfuric acid to obtain 87 g of a product in which the epoxy equivalent was 189 and the EP ratio was 59.7% (yield: 29.8%). The temperature of the reaction solution rose immediately after the start of the reaction, ultimately exceeding 100° C. and resulting in bumping. In addition to forming a gel-like substance, the reaction solution had a brown color. The yield at which the target compound was acquired decreased and EP ratio also decreased.

Comparative Example 2

A glycidylation reaction was carried out in the same manner as Example 1 with the exception of doubling the amount of sulfuric acid added in the sulfuric acid addition step in all of the addition steps (19.0 g (67.1 mmol)). The pH of the reaction solution when all of the sulfuric acid had been added was confirmed to be 0.8. Following completion of the reaction, 120 g of product (yield: 41.3%) were obtained in which the epoxy equivalent was 197 and the EP ratio was 53.9%. The temperature of the reaction solution rose immediately after the start of the reaction, ultimately exceeding 100° C. and resulting in bumping. In addition to forming a gel-like substance, the reaction solution was discolored to brown. The yield at which the target compound was acquired decreased and PP ratio also decreased. A large amount of a brown gel-like substance precipitated that was thought to be hydrolysates (800 g, with water contained) and it was difficult to extract the target compound from the reaction solution. All of the reaction solution gelled resulting in a viscous sponge-like substance. After filtering out the gel-like substance and sequentially washing with ethyl acetate (500 ml) and methanol (500 ml), the resulting substance was sandwiched between filter paper to absorb the solvent component followed by drying the solid fraction under reduced pressure to obtain a brown solid. Signal data presumed to be able to be assigned to the hydrolysates is as shown below.

$^1$H-NMR {400 MHz, DMSO-d$_6$, 27° C.} δ1.60 (6H, s, CH$_3$), δ3.3-3.5 (2H, brm, PhCH$_2$CH(O$\underline{H}$)CH$_2$(O$\underline{H}$), PhOCH$_2$CH(O$\underline{H}$)CH$_2$(O$\underline{H}$)), δ3.6 (2H, brm, PhCH$_2$CH(OH)C$\underline{H}_2$(OH)), δ3.8 (2H, m, PhOCH$_2$CH(OH)C$\underline{H}_2$(OH)), δ3.9 (2H, brm, PhOCH$_2$C$\underline{H}$(OH)CH$_2$(OH)), δ4.4 (2H, brm, PhCH$_2$C$\underline{H}$(OH)CH$_2$(OH)), δ4.6 (2H, brm, PhOC$\underline{H}_2$CH(OH)CH$_2$(OH)), δ4.9 (2H, brm, PhC$\underline{H}_2$CH(OH)CH$_2$(OH)), δ6.8 (brm, 2H, aromatic), δ6.9-7.1 (m, 4H, aromatic).

INDUSTRIAL APPLICABILITY

According to the method for producing a polyvalent glycidyl compound of the present invention, a substituted or unsubstituted polyvalent glycidyl compound can be safely produced from a reaction between a substituted or unsubstituted 2-alkenyl ether compound having two or more substituted or unsubstituted 2-alkenyl groups in a molecule thereof and a hydrogen peroxide aqueous solution at high yield (by inhibiting hydrolysis of glycidyl ether groups) and at low cost by a simple procedure, thereby making this method industrially useful.

The invention claimed is:
1. A method for producing a polyvalent glycidyl compound comprising: oxidizing a 2-alkenyl ether compound having two or more substituted or unsubstituted 2-alkenyl groups and one or more substituted or unsubstituted 2-alkenyl ether groups in a molecule thereof in a reaction solution comprising the 2-alkenyl ether compound, catalysts in the form of a tungsten compound and a quaternary ammonium salt, and a co-catalyst in the form of phosphoric acid,
   wherein a step of adding a hydrogen peroxide aqueous solution to the reaction solution and a step of adding an acid other than phosphoric acid to the reaction solution to control the pH of the reaction solution to 1.0 to 4.0 are alternately repeated multiple times.
2. The method for producing a polyvalent glycidyl compound according to claim 1, wherein the step of adding the hydrogen peroxide aqueous solution and the step of adding the acid other than phosphoric acid are repeated 2 to 20 times during the reaction at an interval of 0.1 hour to 1 hour each time.
3. The method for producing a polyvalent glycidyl compound according to claim 1, wherein the step of adding the hydrogen peroxide aqueous solution and the step of adding the acid other than phosphoric acid are repeated at least twice until the total amount of the hydrogen peroxide aqueous solution added to the reaction solution reaches 0.5 equivalents relative to the total amount of carbon-carbon double bond of the 2-alkenyl groups and 2-alkenyl ether groups of the 2-alkenyl ether compound.
4. The method for producing a polyvalent glycidyl compound according to claim 1, wherein the step of adding the hydrogen peroxide aqueous solution to the reaction solution and the step of adding the acid other than phosphoric acid are carried out so that the temperature of the reaction solution does not exceed 50° C.
5. The method for producing a polyvalent glycidyl compound according to claim 1, wherein the 2-alkenyl ether compound contains an aromatic ring in a molecule thereof, and has one or more substituted or unsubstituted 2-alkenyl ether groups directly bonded to the aromatic ring and two or more substituted or unsubstituted 2-alkenyl groups directly bonded to the aromatic ring, and the substituted or unsubstituted 2-alkenyl groups are located at the ortho position or para position relative to the substituted or unsubstituted 2-alkenyl ether groups.
6. The method for producing a polyvalent glycidyl compound according to claim 1, wherein the 2-alkenyl ether compound is a compound represented by formula (1):

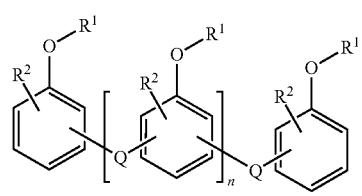

wherein R$^1$ and R$^2$ respectively and independently represent a group represented by the following formula (2), Q respectively and independently represents an alkylene group represented by the formula —CR$^3$R$^4$—, cycloalkylene group having 3 to 12 carbon atoms, arylene group composed of a single aromatic ring having 6 to 10 carbon atoms or arylene group obtained by linking two to three aromatic rings having 6 to 10 carbon atoms, divalent aliphatic condensed ring having 7 to 12 carbon atoms or divalent group comprising a combination thereof, R$^3$ and R$^4$ respectively and independently represent a hydrogen atom, alkyl group having 1 to 10 carbon atoms, alkenyl group having 2 to 10 carbon atoms, cycloalkyl group having 3 to 12 carbon atoms or aryl group having 6 to 10 carbon atoms, n represents an integer of 0 to 50, and R$^5$, R$^6$ and R$^7$ in formula (2) respectively and independently represent a hydrogen atom, alkyl group having 1 to 10 carbon atoms, cycloalkyl group having 3 to 12 carbon atoms or aryl group having 6 to 10 carbon atoms, or a compound having a naphthalene ring instead of the benzene ring of formula (1);

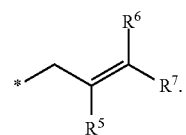

7. The method for producing a polyvalent glycidyl compound according to claim 6, wherein in formula (1),
Q is —C(CH$_3$)$_2$— and n is 0; or
Q is —(CH$_2$)—, —CH(Ph)-, —CH$_2$-Ph-Ph-CH$_2$—, —CH$_2$-Ph-CH$_2$—, a divalent unsubstituted tetrahydrodicyclopentadiene ring or a divalent unsubstituted tetrahydrodicyclopentadiene ring having —CH$_2$— bonded to both ends, wherein Ph is an unsubstituted benzene ring, and n is an integer of 0 to 50, and R$^2$ is located at the ortho position or para position relative to OR$^1$.

8. The method for producing a polyvalent glycidyl compound according to claim 1, wherein the tungsten compound is any of a mixture of sodium tungstate and tungstic acid, a mixture of sodium tungstate and a mineral acid or a mixture of tungstic acid and an alkaline compound.

9. The method for producing a polyvalent glycidyl compound according to claim 1, wherein the total number of carbon atoms of the four substituents bonded to the nitrogen atom of the quaternary ammonium salt is 6 to 50.

10. The method for producing a polyvalent glycidyl compound according to claim 1, wherein the acid other than phosphoric acid is at least one type of mineral acid selected from the group consisting of polyphosphoric acid, pyrophosphoric acid, sulfonic acid, nitric acid, sulfuric acid, hydrochloric acid and boric acid, or is at least one type of organic acid selected from the group consisting of benzenesulfonic acid, p-toluenesulfonic acid, methanesulfonic acid, trifluoromethanesulfonic acid and trifluoroacetic acid.

11. The method for producing a polyvalent glycidyl compound according to claim 2, wherein the step of adding the hydrogen peroxide aqueous solution and the step of adding the acid other than phosphoric acid are repeated at least twice until the total amount of the hydrogen peroxide aqueous solution added to the reaction solution reaches 0.5 equivalents relative to the total amount of carbon-carbon double bond of the 2-alkenyl groups and 2-alkenyl ether groups of the 2-alkenyl ether compound.

12. The method for producing a polyvalent glycidyl compound according to claim 10, wherein the acid other than phosphoric acid is sulfuric acid.

\* \* \* \* \*